(12) United States Patent
Mosjidis et al.

US007615240B2

(10) Patent No.: US 7,615,240 B2
(45) Date of Patent: Nov. 10, 2009

(54) METHOD AND COMPOSITION FOR THE CONTROL OF GASTROINTESTINAL PARASITES IN ANIMALS

(75) Inventors: Jorge A. Mosjidis, Auburn, AL (US); Thomas H. Terrill, Macon, GA (US); James E. Miller, Baton Rouge, LA (US); Joan M. Burke, Greenwood, AR (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 11/327,066

(22) Filed: Jan. 6, 2006

(65) Prior Publication Data
US 2006/0153901 A1 Jul. 13, 2006

Related U.S. Application Data

(60) Provisional application No. 60/642,253, filed on Jan. 7, 2005.

(51) Int. Cl.
*A61K 36/48* (2006.01)
*A61K 36/00* (2006.01)

(52) U.S. Cl. ........................... 424/757; 424/725

(58) Field of Classification Search .......... None
See application file for complete search history.

(56) References Cited

U.S. PATENT DOCUMENTS

| 2,841,496 | A | * | 7/1958 | Brockman | 426/630 |
| 3,155,521 | A | * | 11/1964 | Ward et al. | 514/311 |
| 5,651,550 | A | * | 7/1997 | LaVorgna et al. | 273/363 |
| 5,837,257 | A | * | 11/1998 | Tsai et al. | 424/741 |
| 5,863,775 | A | * | 1/1999 | Atkinson et al. | 424/94.1 |
| 6,168,803 | B1 | * | 1/2001 | Harris et al. | 424/442 |
| 2006/0003064 | A1 | * | 1/2006 | James | 426/481 |

OTHER PUBLICATIONS

Lema N. "Sheep and Goat Nutrition Guideline", Department of Food and Animal Science. Alabama A&M University [online] May 7, 2001 [retrieved on Sep. 30, 2008] Retrieved form the Internet: <http://web.archive.org/web/20010507212039/http://www.aces.edu/dept/extcomm/newspaper/sheep-goat.html>.*
Kirsch et al. "Laboratory Investigations in Sheep with a New Anthelmintic". Vet. Rec. vol. 97, No. 2 (1975) 28-31, Abstract only.*
Williams et al. J. Nutrition. 1940. vol. 40, No. 3, pp. 251-262.*

Haenlein, G.F.W. 1992. "Alternatives in Dairy Product Market," Proc. Sheep and Goat Industry Devel. Symp. (A.D. Scarfe. ed.), Tuskegee University, AL.
Haslem, E. 1989 "Plant Polyphenols—Vegetable Tannins," Cambridge University Press, U.K.
Min, B.R., W.C. McNabb, T.N. Barry, P.D. Kemp, G.C. Waghorn, M.F. McDonald, 1999 "The Effect of Condensed Tannins in *Lotus corniculatus* Upon Reproductive Efficiency and Wool Production in Sheep During Late Summer and Autumn," J. Agric. Sci. 132, 323-334.
Niezen, J.H., T.S. Waghorn, W.A.G. Charleston, G.C. Waghorn, 1995 "Growth and Gastrointestinal Parasitism in Lambs Gracing One of Seven Herbages and Dosed with Larvae for Six Weeks," J. Argic. Sci. 125, 281-289.
Hansen, J. and B. Perry, 1994 "The Epidemiology, Diagnosis and Control of Helminth Parasites of Ruminants: A Handbook. International Livestock Research Institute," Nairobi, Kenya.
Pinkerton, F., E.N. Escobar, L. Harwell, W. Drinkwater, 1994 "A Survey of Prevalent Production and Marketing Practices in Meat Goats of Southern Origin," Langston Univ. Goat Res. Ext. Newsletter 182, 1-47.
Maxey, K. (1993) "*Year of Progress*". Dairy Goat Journal, 11, 32.
Abascal, Kathy; Ganora, Lisa; and Yarnell, Eric, "The Effect of Freeze-Drying and Its Implications for Botanical Medicine: A Review", Phytother, Res. 19, pp. 655-660 (2005).
Terrill, T. H.; Windham, W. R.; Evans, J. J.; and Hoveland, C. S., "Condensed Tannin Concentration in Sericea Lespedeza as Influenced by Preservation Method", Crop Sci. 30, pp. 219-224 (1990).
Terrill, T. H.; Windham, W. R.; Hoveland, C. S.; and Amos, H. E., "Forage Preservation Method Influences on Tannin Concentration, Intake, and Digestibility of Sericea Lespedeza by Sheep", Agron. J. 81, pp. 435-439 (1989).
S.A. Shaik, et al "Effects of feeding sericea lespedeza hay to goats Infected with *Haemonchus contortus*." South African Journal Animal Science 34(Suppl. 1), 234-236, 2004.
J.A. Mosjidis et al. "Sericea Lespedeza, an Anthelmintic Plant for Goats with Great Potential in Pasture Renovation and in Pure Stands." Proceedings of the Joint Meeting of the 39th North American Alfalfa Improvement Conference, Quebec City, Quebec, Canada, Jul. 18-21.

(Continued)

*Primary Examiner*—Christopher R. Tate
(74) *Attorney, Agent, or Firm*—Andrus, Sceales, Starke & Sawall, LLP

(57) ABSTRACT

The present invention provides methods and compositions for controlling gastrointestinal parasitic infections in animals. More specifically, the invention involves the use of *sericea lespedeza* (*Lespedeza cuneata*), commonly referred to as Chinese bush clover, in the diet of animals to control nematodal gastrointestinal infections.

31 Claims, 9 Drawing Sheets

OTHER PUBLICATIONS

S. Athanasiadou et al. "Consequences of long-term feeding with condensed tannins on sheep parasitised with *Trichostrongylus colubriformis*." International Journal for Parasitology. 30(2000):1025-1033.

H.A. Glimp et al. "Strategies for Expanding Goat Meat Production, Processing, and Marketing in the Southeastern United States." 1986, Winrock International, Morrilton, AR.

P. Hördegen, et al. "The anthelmintic efficacy of five plant products against gastrointestinal trichostrongylids in artificially infected lambs." Vet Parasitology, 117:51-60, (2003).

Q.A. McKellar "Exotoxicology and residues of anthelmintic compounds." Vet Parasitology 117:51-60, 1997.

B.R. Min et al. "Tannins for suppression of internal parasites." J.Anim. Sci. 81(E.Suppl.2):E102-E109: 2003.

L.L. Mortensen, et al. "Evaluation of prevalence and clinical implications of anthelmintic resistance in gastrointestinal nematodes in goats." JAVMA 223:495-500 (Aug. 15, 2003).

J.H. Niezen et al., 1998 "Production, faecal egg counts and worm burdens of ewe lambs which grazed six contesting forages." Vet Parasitology, 80:15-27: 1998.

V. Paolini, et al. 2003 "Effects of condensed tannins on goats experimentally infected with *Haemonchus contortus*." Vet Parasitology, 113(2003): 253-261.

V. Paolini, et al. 2003 "Effects of sainfoin hay on gastrointestinal nematode infections in goats." The Veterinary Record 152:600-601.

R. Pritchard, 2001 "Anthelmintic resistance on goat farms in Georgia: efficancy of anthemelmintics against gastrointestinal nemotaodes in two selected goat herds" Vet Parasitology 97:259-268.

A. Zajac et al. 2000 "Multiple anthelmintic resistance in a goat herd." Vet Parasitology 87:163-172.

Aerts, R.J. et al. 1999 "Condensed tannins from *Lotus corniculatus* and *Lotus pedunculatus* exert different effects on the in vitro rumen degradation of ribulose 1,5-bisphosphate corboxylase (Rubisco) protein." J. Sci. Food Agric. 79, 79-85.

T.N. Barry, et al. 1986 "Interrelationships between the concentrations of total condensed tannin, free condensed tannin and lignin in *Lotus* sp. and their possible consequences in ruminant nutrition." J. Sci Food Agric. 37, 248-254.

T.N. Barry, et al. 2001 "Plant secondary compounds; their impact on nutritive value and upon animal production." Proc. XIX Int. Grass Conf, Sao Paulo, Brazil, pp. 445-452.

R.E. Burns, 1966 "Tannin in sericea lespedeza." Bull. 164, Georgia Agric. Experiment Stations, Athens, Georgia.

J.M. Burke, et al. 2004 "Effect of copper oxide wire particles dosage and feed supplement level on *Haemonchus contortus* infection in lambs." Vet Parasitology, 123:235-243.

C. Chartier et al. 2000 "Efficacy of copper oxide needles for the control of nematode parasites in dairy goats." Vet. Research Communication 24:389-399.

L.Y. Foo et al. 1997 "Proanthocyanidins from *Lotus pedunculatus*." Phytochemistry, vol. 45:1689-1696.

L.Y. Foo et al. 1997 "Proanthocyandins from *Lotus corniculatus*." Phytochemisty, vol. 41:617-621.

B.R. Min, et al. 2005 "The effect of grazing forage containing condensed tannins on gastro-intestinal parasite infection and milk composition in Agora does," Veterinary Parasitology, 130: 105-113.

R. Stevens 2000 "Sericea Lespedeza" Plant of the Month, Mar. 2000; Noble Foundation http://www.noble.org/Ag/PlantOfMonth/sericea-lespedeza/.

C. O'H. Mosjidis, et al. 1990 "Developmental Differences in the Location of Polyphenols and Condensed Tannins in Leaves and Stems of Sericea Lespedeza, *Lespedeza cuneata*," Annals of Botany, 65: 355-60.

C.S. Hoveland, et al. 1990 "Sericea lespedeza production in Georgia." The Georgia Experiment Stations Research. Bull. 393.

C. Kahiya, et al. 2003 "Effects of *Acacia nilotica* and *Acacia karoo* diets on *Haemonchus cantortus* infection in goats." Vet. Parasitol 115:265-274.

D.P. Knox, 2000 "Development of vaccines against gastrointestinal nematodes." Vet. Parasitol 120:43-61.

D.P. Knox et al. 2001 "Vaccination against gastrointestinal nematod parasites of ruminants using gut-expressed antigens." Vet. Parasitol. 100:21-32.

K. Lange et al. 2005 "Effect of the condensed tannin-containing forage, sericea lespedeza, fed as hay, on natural and experimental challenge infection in lambs." Abst. Southern Sec. ASAS Meetings, Little Rock, AR pp. 15-16.

M. Larsen 2000 "Prospects for controlling animal parasitic nematodes by predacious micro fungi." Parasitol 120:S120-S131.

J.E. Miller 1995 "Parasites Affecting Goats in the Southeast," Goat Production and Marketing Opportunities in the South, Conference Proceedings, Aug. 19, 1995, Louisiana State University, Alexandria, Louisiana, pp. 99-104.

Conservation Commission of Missouri, 2004 "Sericea Lespedeza [*Lespedeza cuneata* (*Dum.-Cours*) *Don*] Species Character." Vegetation Management Guideline, http://www.conservation.state.mo.us/nathis/exotic/vegman/twentytw.htm.

B.R. Min et al. 2004 "The effect of short-term consumption of a forage containing condensed tannins on gastrointestinal nematode parasite infections in grazing wether goats." Small Rumin. Res. 51, 279-283.

A.L. Molan et al. 1999 "Condensed tannins and gastro-intestinal parasites in sheep." Proc. NZ Grassl. Assoc. 61, 57-61.

A.L. Molan et al. 2000 "The effect of condensed tannins from seven herbages on *Trichostrongylus colubriformis* larval migration in vitro." Folia Parasitol 47:39-44.

J.A. Mosjidis 2001 "Registration of 'AU Grazer' Sericea Lespedeza." Crop Science, 41:262 http://crop.scijournals.org/egi/content/full/41/1/262.

J.H. Niezen et al. 2002 "The effect of feeding sulla (*Hedysarum coronarium*) or Lucerne (*Medicago sativa*) on lamb parasite burdens and development of immunity to gastrointestinal nematodes." Vet. Parasitol. 105,229-245.

Virginia Tech Weed ID Guide "Sericea Lespedeza: *Lespedeza cuneata*." http://www.ppws.vt.edu/scott/weed_id/lescu.htm, downloaded 2005.

P. Ohlenbusch et al. "Sericea Lespedeza: History, Characteristics, and Identification." Kansas State Univ., Mar. 2001.

L. Augsten et al. 2003 "Digestive Anatomy in Ruminants," Hypertexts for Biomedical Sciences, Feb. 23, 2003, <http://arbl.cvmbs.colostate.edu/hbooks/pathphys/digestion/herbivorces/rumen_anat.html>.

S.A. Shaik et al. 2004 "Effects of feeding sericea lespedeza hay to goats infected with *Haemonchus contortus*." SAJ Anim. Sci. 34, 234-236.

T.H. Terrill et al. 2001 "Anthelmintic resistance on goat farms in Georgia:efficacy of anthelmintics against gastrointestinal nematodes in two selected goat herds." Vet. Parasitol. 97, 261-268.

T.H. et al. 2004 "Capability of the nematode-trapping fungus *Duddingtonia flagrans* to reduce infective larvae of gastrointestinal nematodes in goat feces in the southeastern United States: dose titration and dose time interval studies." Vet. Parasitol. 120, 285-296.

T.H. Terrill et al. 1992 "Determination of extractable and bound condensed tannin concentrations in forage plants, protein concentrate meals, and cereal grains." J. Sci. Food Agric. 58, 321-329.

T.H. Terrill et al. 1989 "Influence of forage preservation method on tannin concentration, intake and digestibility of sericea lespedeza by sheep." Agron. J. 81, 435-439.

\* cited by examiner

METHOD AND COMPOSITION FOR THE CONTROL OF GASTROINTESTINAL PARASITES IN ANIMALS

CROSS REFERENCE TO RELATED APPLICATION

This application claims priority to Provisional Application No. 60/642,253, filed Jan. 7, 2005.

This invention was made with United States Government support awarded by the USDA, Southern SARE, Grant #LS02-143. The United States Government has certain rights in this invention.

BACKGROUND OF THE INVENTION

The present invention relates to controlling gastrointestinal parasitic infections in animals, and more particularly to methods and compositions for controlling gastrointestinal nematodal infections in animals, especially ruminants.

In the southern USA, goat production for meat or milk is an attractive alternative enterprise for farmers because of comparatively low cost of breeding stock, high reproductive rate of goats, and their ability to thrive on native pastures or brushland that is unsuitable for cropping (Glimp et al, 1896, "Strategies for Expanding Goat Meat Product Processing, and Marketing in the Southeastern US", Winrock International, Morrilton, Ark.). In addition, there is high ethnic demand for goat meat and milk products in the USA, particularly in large metropolitan areas, which is exceeding current production levels. Despite increasing demand for goat products, growth of the goat industry in the southern USA has been slow. The major hindrance to economic goat production in this region is infection with gastrointestinal nematodes (GIN), particularly *Haemonchus contortus*. The conventional method of GIN control by farmers in the Southeast is regular use of anthelmintics, sometimes monthly or more during the warm season. Overuse and/or misuse of anthelmintics has led to increased anthelmintic resistance in GIN of goats, sheep, and cattle in many parts of the world (Prichard, 1994. "Anthelmintic Resistance", Vet. Parasitol, 54:259-268), and recent reports from Virginia (Zajac et al, 2000, "Multiple Anthelmintic Resistance in a Goat Herd". Vet. Parasitol. 87:163-172) and Georgia (Mortensen et al, 2003. "Evaluation of Prevalence and Clinical Implications of Anthelmintic Resistance in Gastrointestinal Nematodes in Goats". JAVMA 223:495-500) indicate that anthelmintic resistance in goats has become highly prevalent in the southern USA.

In traditional veterinary medicine, which is still practiced in many parts of the world, the use of plants with anthelmintic properties has been considered as an alternative to anthelmintic drugs. Grazing forages high in tannins or adding purified condensed tannins (CT) to the diet has been shown to reduce parasite eggs in sheep and goat feces in a number of studies (Niezen et al, 1998; "Production, Fecal Egg Counts and Worm Burdens of Ewe Lambs which Grazed Six Contrasting Forages". Vet. Parasit. 80:15-27; Athanasiadou et al, 2000; "Consequences of Long-Term Feeding with Condensed Tannins on Sheep Parasitized with *T. colubriformis*". Int. J. Parasitol. 30:1025-1033; Min et al, 2003. "Tannins for Suppression of Internal Parasites". J. Anim. Sci. 81 (E. Suppl. 2). E102-E109; Paolini et al, 2003, "Effects of Condensed Tannins on Goats Experimentally Infected with *Haemonchus contortus*", Vet. Parasit. 113:253-261.). Paolini et al, 2003, "Effects of Sainfoin Hay on Gastrointestinal Nematode Infections in Goats", Vet. Record 152:600-601 reported lower egg count in feces of goats fed sainfoin (*Onobrychi viciifolia* Scop.) hay compared with grass hay, but the anthelmintic effects of feeding hay from CT-containing forages is not well documented.

SUMMARY OF THE INVENTION

The present invention provides methods and compositions for controlling gastrointestinal parasitic infections in animals. More specifically, the invention involves the use of *sericea lespedeza* (*Lespedeza cuneata*), commonly referred to as Chinese bush clover, in the diet of animals to control nematodal gastrointestinal infections.

In one embodiment, the invention provides an animal feed composition comprising a diet containing meal, and an effective amount of *sericea lespedeza* hay for controlling gastrointestinal nematode infections in animals. An effective amount comprises about 0.2 kg per kg of diet to about 1.0 kg per kg of diet, preferably from about 0.25 kg per kg of diet to about 0.8 kg per kg of diet, and most preferably from about 0.5 kg per kg of diet to about 0.75 kg per kg of diet, on a dry weight basis.

In another embodiment, the invention provides a method of controlling gastrointestinal nematode infections in animals, comprising the steps of providing an animal feed comprising a diet containing meal, incorporating with said diet an effective amount of *sericea lespedeza* hay for controlling gastrointestinal nematode infections to form a feed mixture, and feeding said feed mixture to an animal.

In yet another embodiment, the invention provides a method of compounding feed for animals, comprising the steps of providing an animal feed comprising a diet containing meal, incorporating with said meal an effective amount of *sericea lespedeza* hay for controlling gastrointestinal nematode infections to form a feed mixture, and forming said feed mixture into a discrete shape.

The advantages and utility of this invention are significant. Infection with gastrointestinal nematodes, particularly *Haemonchus contortus*, is a major limiting factor to economic goat and sheep production in the southern USA. Recent reports indicate that anthelmintic resistance in goats and sheep has become highly prevalent in the southern USA. The use of *sericea lespedeza* as an alternative to and/or in addition to pharmaceutical anthelmintic drugs to reduce gastrointestinal nematode infections in animals, especially small ruminants will have a major positive impact on the economics of raising sheep and goats. Other advantages are ease of application, cost-effectiveness, and "all-natural" label of the *sericea lespedeza* cultivars.

DETAILED DESCRIPTION OF THE INVENTION

Figure 1:
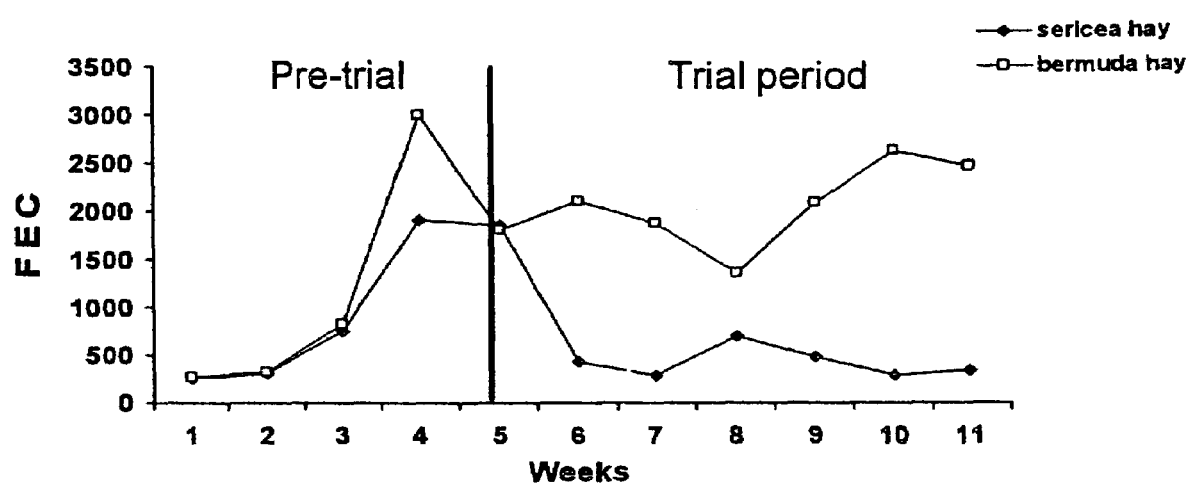
FIG. 1 is a graph of fecal egg count over time comparing the results of feeding either Bermuda grass hay or *sericea lespedeza* hay to goats infected with the nematode *Haemonchus contortus* in the experiment described in Example 1 herein.
Figure 2:
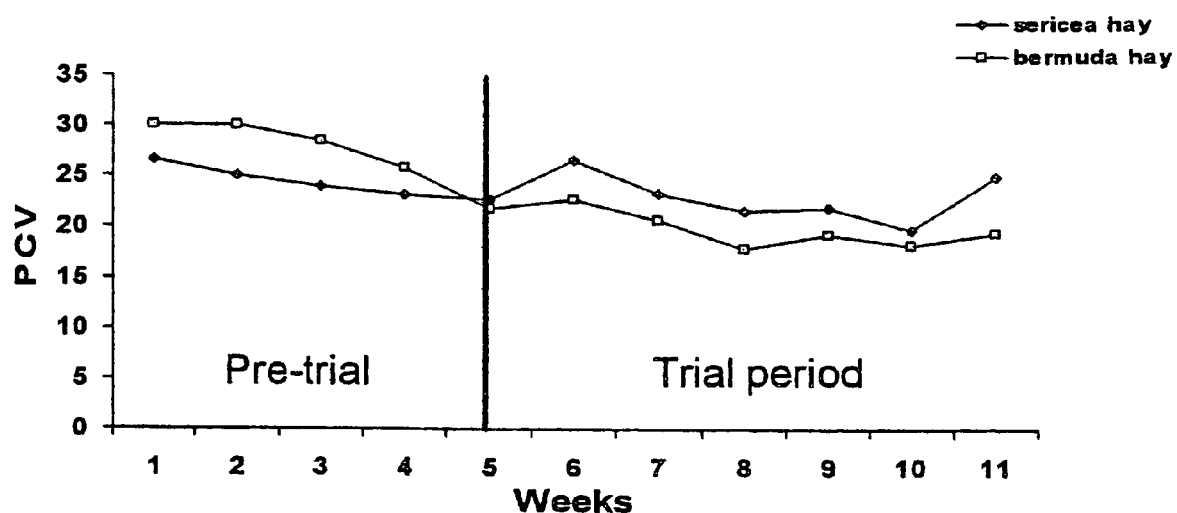
FIG. 2 is a graph illustrating blood packed cell volume over time comparing the results of feeding either Bermuda grass hay or *sericea lespedeza* hay to goats infected with the nematode *Haemonchus contortus* in the experiment described in Example 1 herein.

The present invention provides an animal feed containing *sericea lespedeza* either as the sole active ingredient, or in combination with an anthelmintic agent, to accomplish the improved results disclosed herein, i.e. controlling gastrointestinal parasitic infections in animals. The use of *sericea lespedeza* hay in animal feeds controls gastrointestinal parasitic infections, especially nematode infections. It is believed that *sericea lespedeza* acts via one or more of the following mechanisms: (1) by directly reducing the number of worms once the hay is ingested by the animal; (2) by directly reducing the rate of larval development once ingested by the animal; (3) by decreasing the fecundity of female worms; and/or (4) by either reducing fecundity or reducing the number of female worms, the number of eggs passed in the animals feces is correspondingly decreased resulting in lower pasture contamination with the result of decreased reinfection rates in grazing animals. As a result, the use of *sericea lespedeza* hay in animal feed will result in a severe reduction of, and possibly the complete elimination of, the need for synthetic deworming anthelmintic agents.

*Sericea lespedeza* is an aggressive warm season perennial legume in the family Febaceae/Leguminosae. *Sericea lespedeza* is also commonly referred to as Chinese bush clover, silky bush clover, or Himalayan bush clover. The scientific name of *sericea lespedeza* is *Lespedeza cuneata*. *Sericea lespedeza* was introduced from Asia for use as forage and hay production on poor soils, and for erosion control in the southeastern United States. It can flourish where other plants have difficulty growing, such as on eroded, infertile soils. It is drought resistant, is rarely bothered by insects or disease, produces numerous seed and abundant forage, and is a long lived perennial. It contains approximately 52 grams of condensed tannins (CT) per kg, but the CT content thereof may be quite variable depending on environmental conditions, plant tissue sampled, extraction method used, and the plant sampled within a cultivar.

*Sericea lespedeza* has been recognized as quality forage due to its high levels of crude protein. However, high tannin concentrations significantly reduce beef cattle grazing of *sericea lespedeza*. Livestock typically do not like to graze *sericea lespedeza* because it is relatively high in tannins. High levels of tannins may cause *sericea lespedeza* to be unpalatable and reduce digestibility. The level of tannins in *sericea lespedeza* appear to increase with maturity of the plant, high air temperatures, and lower rain fall. Sheep and goats will more readily select and consume fresh *sericea lespedeza* forage than cattle. However, it has been observed that cattle, sheep and goats will more readily consume *sericea lespedeza* hay since field drying decreases the extractable tannin concentration.

As noted above, *sericea lespedeza* contains a significant amount of condensed tannins. Tannins are plant polyphenols that bind and precipitate proteins. These large polyphenolic compounds contain sufficient hydroxyls and other substitutions such as carboxyls to form strong complexes with proteins and other macromolecules. Tannins have a molecular weight ranging from 500 to over 20,000. Tannins are usually divided into hydrolyzable tannins and condensed tannins (proanthocyanidins). Condensed tannins, also known as proanthocyanidins, are polymers of 2 to 50 or more flavonoid units that are joined by carbon carbon bonds which are not susceptible to being cleaved by hydrolysis. This results in the reduced digestibility of plants containing high levels of tannins.

There are numerous species of gastrointestinal parasites in animals. It is believed that *sericea lespedeza* will be effective in controlling gastrointestinal nematode infections of the following genera: *Toxocara, Toxascaris, Physaloptera, Ancylostoma, Uncinaria, Dipylidium, Hydatigena,* and *Trichuris* in feline; *Toxocara, Toxascaris, Physaloptera, Spirocerca, Ancylostoma, Uncinaria, Dipylidium, Taenia, Strongyloides,* and *Trichuris* in canine; *Anoplocephala, Draschia, Habronema, Trichostrongylus, Parascaris, Strongyloides, Strongylus, Oxyuris,* and *Probstmayria* in equine; *Haemonchus, Ostertagia, Telodorsagia, Trichostrongylus, Cooperia, Moniezia, Bunostomum, Nematodirus, Toxocara, Strongyloides, Oesophagostomum, Trichuris, Marshallagia, Chabertia, Skrjabinema,* and *Spirculoptertagia* in ruminants; *Ascarops, Hyostrongylus, Physocephalus, Trichostrongylus, Macracanthorhynchus, Diphyllobothrium, Ascaris, Strongyloides, Trichuris,* and *Oesophagostomum* in swine; *Capillaria, Gongylonema, Tetramaeres, Davainea, Hymenolepis, Raillietina, Ascardia, Capillaria, Strongyloides, Trichostrongylus,* and *Heterakis* in poultry; *Obeliscoides, Nematodirus, Trichostrongylus, Passalurus,* and *Trichuris* in laboratory rabbits; *Syphacia, Aspicularis, Nippostrongylus, Hymenolepis, Taenia, Moniliformis,* and *Heligmosomoides* in laboratory rodents; and all of the aforementioned nematodes included under all of the aforementioned animal groups in exotic hoofstock and zoo animals.

*Sericea lespedeza* is particularly effective in controlling nematodes in ruminants. Of the above genera found in ruminants, *Haemonchus* is the most pathogenic worm of all gastrointestinal parasitic nematodes. Adult worms of the *Haemonchus* genera are the largest nematodes found in the abomasums and small intestines of ruminants such as sheep and goats and measure about 1 to 3 centimeters long. They feed on blood and thus will have a red color due to the blood in the intestine. Adult worms has a lancet in their mouth which they use to open blood vessels to obtain food. Each adult will lead to the loss of about 0.05 mm of blood per day. The females are prolific egg layers. The life cycle is direct and can be completed in 2-5 weeks. Gastrointestinal parasites such as the above nematodes are a significant problem in ruminants because unless they are controlled, the animals become anemic, weak, and sometimes die. Control of such parasites has traditionally been via the use of synthetic anthelmintic deworming treatments, but worms have readily developed resistance to most synthetic anthelmintics. Applicant has thus discovered that *sericea lespedeza* hay provides an alternative, "all-natural", sustainable method of worm control.

In order to accomplish the desired results of reducing and/or eliminating gastrointestinal nematode infections, the animals diet should contain *sericea lespedeza* hay in an amount from about 0.2 kg per kg of diet to about 1.0 kg per kg of diet, on a dry weight basis. Preferably, the diet should contain about 0.25 kg per kg of diet to about 0.8 kg per kg of diet, on a dry weight basis, and most preferably from about 0.5 kg per kg of diet to about 0.75 kg per kg of diet, on a dry weight basis. The preferred *sericea lespedeza* variety is AU Grazer, but other varieties such as Serala, Interstate, Interstate 76, AU Lotan, or AU Donnelly could also be utilized.

The *sericea lespedeza* hay may be administered or fed to animals either alone or in combination with conventional animal feed and/or other feed additive agents. Thus, the *sericea lespedeza* hay can be readily administered or fed to animals either by mixing it directly into animal feed or separately from the animal feed as an additive or supplement. If formulated as an additive, the additive itself may be then mixed with the conventional animal feed or fed separately. The desired proportions of *sericea lespedeza* hay in animal feed is dependent upon the particular parasitic infection being addressed and the degree of response desired, but a sufficient amount should be utilized to be effective to reduce the number of nematodes, the rate of larval development, and/or fecundity of female nematodes. It should be understood that the specific amount of *sericea lespedeza* hay fed to an animal in any given case will be determined and adjusted in accordance with the animal being treated, the problem to be treated, the condition of the animal and other relevant facts that may modify the activity of *sericea lespedeza* hay or the response of the animal, as is well known by those skilled in the art of animal husbandry. In addition, either a single daily dose or multiple daily dosages of *sericea lespedeza* hay may be fed.

The animal feed may be any protein containing meal normally employed to meet the dietary requirements of the animal. Many of such protein containing meals are typically primarily composed of grasses, grains such as barley, oats, wheat or corn, soybean meal or a corn/soy meal mix. For example, a typical commercially available meal product fed to cattle is 4-Square Stocker/Grower Supreme 12N available from Purina. A typical commercially available meal product fed to goats is Goat Chow available from Purina. A typical commercially available meal product fed to sheep is Lamb & Sheep Feed, available from Nutrena. Each of these commercially available meal products are typical examples of animal feeds with which the *sericea lespedeza* hay may be incorporated to treat gastrointestinal nematode infections. Thus, any type of protein containing meal may be utilized as the base mix to which the *sericea lespedeza* hay may be incorporated.

The animal feed may also include adjuvants, such as binders, preserving agents, etc. It may also contain other therapeutically valuable substances such as synthetic anthelmintic drugs, such as fenbendazole, ivermectin, doramectin, mixodectin, levamisole and albendazole, as well as other commonly used anthelmintic agents, all of which have been traditionally used to deworm animals.

The present invention is applicable to the diet of numerous animals, which herein is defined as including ruminants, pseudo ruminants, laboratory mammals, domestic mammals, exotic hoofstock, poultry, horses and swine. Ruminants include cattle, sheep, goats, bison and deer. Pseudo ruminants include camels, llamas, alpacas and vicunas. Exotic hoofstock include giraffe, black buck antelopes, kudu and zebra. Laboratory mammals include rodents such as rats, mice, hamsters and gerbils, as well as rabbits, while domestic mammals include animals such as cats and dogs. Commercially significant poultry include chickens, turkeys, ducks, geese, pheasants and quail.

The present invention thus relates to an animal feed composition and a method of compounding an animal feed utilizing *sericea lespedeza* hay to control gastrointestinal parasitic infections in animals. In the method of compounding feed for animals in accordance with the present invention, the *sericea lespedeza* hay is incorporated with the animal feed in an amount from about 0.2 kg to about 1.0 kg per kg feed, preferably from about 0.25 kg to about 0.8 kg per kg feed, and most preferably from about 0.5 kg to about 0.75 kg per kg feed, on a dry weight basis. The feed mixture may then be fed "as is," i.e. as a meal, to the animal, or may be further processed and formed into desired discrete shapes for packaging and shipping. In general, these discrete shapes may be pellets, cubes, blocks or briquettes formed by known extrusion and/or compacting techniques. The particular processing technique utilized does not affect the performance of the *sericea lespedeza* hay in the animal feed mixture, as long as the temperature used is not too high, i.e. not above about 70° C.

The present invention is more specifically described by the following examples, which are meant to be illustrative only.

EXAMPLE 1

Introduction

The purpose of the current study was to determine potential anthelmintic effects of feeding *sericea lespedeza* hay to goats.

Materials and Methods

Twenty yearling Spanish×Boer×Kiko cross yearling does were fed two diets (n=10) consisting of primarily coarse-ground *sericea lespedeza* or bermudagrass hay in an 8-week confinement study. The diets were balanced for protein and energy with a small amount of supplement (ground corn, soybean mean, poultry fat, trace mineral salt and vitamin premix). The diets were approximately 80% hay and 20% supplement by weight. Prior to starting the trial, the does acquired a low-level natural GIN infection (<200 EPG; 97% *H. contortus*) by grazing native pasture for approximately 6 months. Three weeks before moving the does to the pens (2 pens of 5 animals each for each treatment), infection level of the does was boosted by a one time drench of 10,060 *H. contortus* larvae per animal.

Goats were assigned to treatment groups based upon fecal EPG. After being moved into feeding pens, all the goats were fed ground bermudagrass hay during a 7-day adjustment period, after which two pens of goats were switched to the sericea hay ration. After four weeks on the experimental rations, all of the goats were again given the bermudagrass ration for an additional 3 weeks. The goats were given a small amount of concentrate (as required to balance the two rations for crude protein and energy) daily throughout the trial, with ad libitum access to hay and water. The concentrate feeding was held constant, while the hay ration for each pen was adjusted daily to allow 10% uneaten feed. Throughout the trial, fecal EPG was monitored in all does on a weekly basis (except week 10).

Fecal egg count (EPG) data was analyzed by repeated measures analysis (SAS, 1992). The pre-trial (sampling dates 1-3), experimental (sampling dates 4-8), and post-trial (sampling dates 9 and 11) periods were analyzed separately.

Results

*Haemonchus contortus* egg excretion was similar between the two groups during a 3-week pretrial period (Table 1). During the 4-week experimental period, treatment, time, and treatment×time effects were all significant (P<0.05). Egg excretion was lower (P<0.05) in the sericea-fed group, with the difference increasing over time. After the sericea-fed goats were switched back to bermudagrass, there were no significant differences in egg excretion (Sampling dates 9 and 11), although EPG was numerically lower in animals previously fed sericea.

TABLE 1

Egg excretion in goats given an artificial infection of *H. contortus* larvae and fed diets of ground sericea *lespedeza* or bermudagrass hay and a small amount of concentrates.

| | Sampling times (weeks after parasite challenge)[1] | | | | | | | | | |
|---|---|---|---|---|---|---|---|---|---|---|
| | Pretrial Period[2] | | | Experimental Period[3] | | | | | Post-trial Period[4] | |
| Diet | 1 | 2 | 3 | 4 | 5 | 6 | 7 | 8 | 9 | 11 |
| | Parasite eggs per gram of feces | | | | | | | | | |
| Bermudagrass hay + concentrates | 300 | 179 | 321 | 179 | 357 | 221 | 436$^a$ | 5150$^a$ | 1314 | 514 |
| Sericea *lespedeza* hay + concentrates | 238 | 263 | 88 | 207 | 107 | 64 | 36$^b$ | 729$^b$ | 233 | 0 |
| SE | 139 | 106 | 185 | 49 | 182 | 57 | 85 | 1239 | 530 | 337 |
| Prob for TRT main effect | 0.76 | 0.59 | 0.40 | 0.69 | 0.35 | 0.08 | 0.01 | 0.03 | 0.20 | 0.32 |

[1]A separate statistical analysis was completed for each period (except week 10).
[2]Goats grazed on pasture for three weeks, moved into pens after week 3, fed bermudagrass diets for 1 week.
[3]Half the animals switched to sericea diet after week 4, fed sericea diets through week 8.
[4]After week 8, all animals switched back to bermudagrass diets through week 11.
$^{a,b}$Column means with unlike superscripts differ (P < 0.05).

Discussion

Grazing of tannin-containing forages has been suggested as an alternative to chemical anthelmintics for controlling gastrointestinal nematodes in both sheep and goats (Niezen et al, 1998, "Production, Fecal Egg Counts and Worm Burdens of Ewe Lambs which Grazed Six Contrasting Forages", Vet. Parasit. 80:15-27; Min et al, 2003, "Tannins for Suppression of Internal Parasites", J. Anim. Sci. 81 (E. Supple. 2):E102-E109). There are limitations to this approach, however, particularly the lack of suitable pasture forages that contain significant levels of CT. Based on the results of the current study, feeding hay of CT-containing forages to control gastrointestinal parasitic nematodes appears to be a viable alternative to grazing CT forages for goats. Feeding hay may also allow these benefits to be realized with other ruminant species, such as cattle, sheep, deer and bison, as well as pseudoruminants such as camels, llamas, alpacas and vicunas, and other animals susceptible to gastrointestinal parasitic infections such as horses, swine and exotic hoofstock such as giraffe, black buck, antelopes, kudu and zebra. Cattle and sheep do not like to graze *sericea lespedeza*, but readily consume it as hay (Terrill et al, 1989, "Forage Preservation Method Influences on Tannin Concentration, Intake, and Digestibility of *Sericea Lespedeza* by Sheep", Agron. J. 81:435-489).

Although goats fed the sericea hay had lower egg counts than those fed bermudagrass hay, these differences were not significant after sericea feeding stopped, suggesting a greater effect on worm fecundity than on worm numbers. This is supported by the work of Min et al, 2003, "Tannins for Suppression of Internal Parasites", J. Anim. Sci. 81 (E. Supple. 2):E102-E109, who reported reduced EPG in goats grazing *sericea lespedeza*, but this reduction was quickly lost when the animals were switched to tall fescue pastures. In contrast, Paolini et al, 2003, "Effects of Sainfoin Hay on Gastrointestinal Nematode Infections in Goats", Vet. Record 152:600-601 reported that egg counts remained lower in goats fed hay from sainfoin compared with grass hay for two weeks after sainfoin hay feeding was stopped. These authors suggested a possible effect on worm numbers. The animals used in the current study were from a breeding herd and could not be slaughtered for actual worm counts. Reduced fecundity could have a large effect on reducing pasture contamination, however. Potential anthelmintic properties of *sericea lespedeza* hay in goats needs to be tested when fed as a supplement to naturally-infected animals under grazing conditions.

Conclusions

Feeding hay of *sericea lespedeza* to goats reduced gastrointestinal parasite egg excretion compared with grass hay and is an effective means of reducing egg shedding on pasture.

EXAMPLE 2

Introduction

This study was conducted to evaluate the effect of the condensed tannin (CT) containing forage, *sericea lespedeza* (SL), fed as hay, on primarily the *Haemonchus contortus* worm infection in sheep.

Methods and Materials

Design: Twenty-eight naturally infected lambs were removed from pasture and maintained in cement floored pens. Lambs were randomly allocated based on FEC to one of four treatment groups (7 animals each): Group 1) control, non-CT hay and established infection; Group 2) non-CT hay and dewormed; Group 3) CT hay and established infection; Group 4) CT hay and dewormed. Groups 2 and 4 were dewormed using levamisole and albendazole on two consecutive days (Days −1 and 0). All animals were fed non-CT hay up to Day 14 and then groups 3 and 4 began being fed *sericea lespedeza* CT hay and Groups 1 and 2 continued being fed non-CT hay. All animals received trickle infections of a mixed larval inoculum of 1000 L3 *H. contortus* larvae three times a week for three weeks beginning on day 14. On Day 60, CT hay feeding stopped and those animals were subsequently fed non-CT hay. Three animals from each group were necropsied on Day 75 for worm recovery. Worms were enumerated and identified. The animals selected were the ones with the highest, lowest and median FEC. The data are reported in Table 2 and plotted in the graphs of FIGS. 3, 4 and 5.

FEC: Feces were collected directly from the rectum and processed using the modified McMaster technique. Results are represented as eggs per gram.

Blood packed cell volume (PCV): Blood was collected by jugular venipuncture using 7 ml EDTA vaccutainer tubes. PCV was determined using hematocrit tubes spun in a microhematocrit centrifuge.

Inoculation: L3 larvae (approximately 97% *H. contortus*) were delivered in water solution by mouth using a 10 ml syringe with metal drenching adaptor.

Results and Discussion

Figure 3:
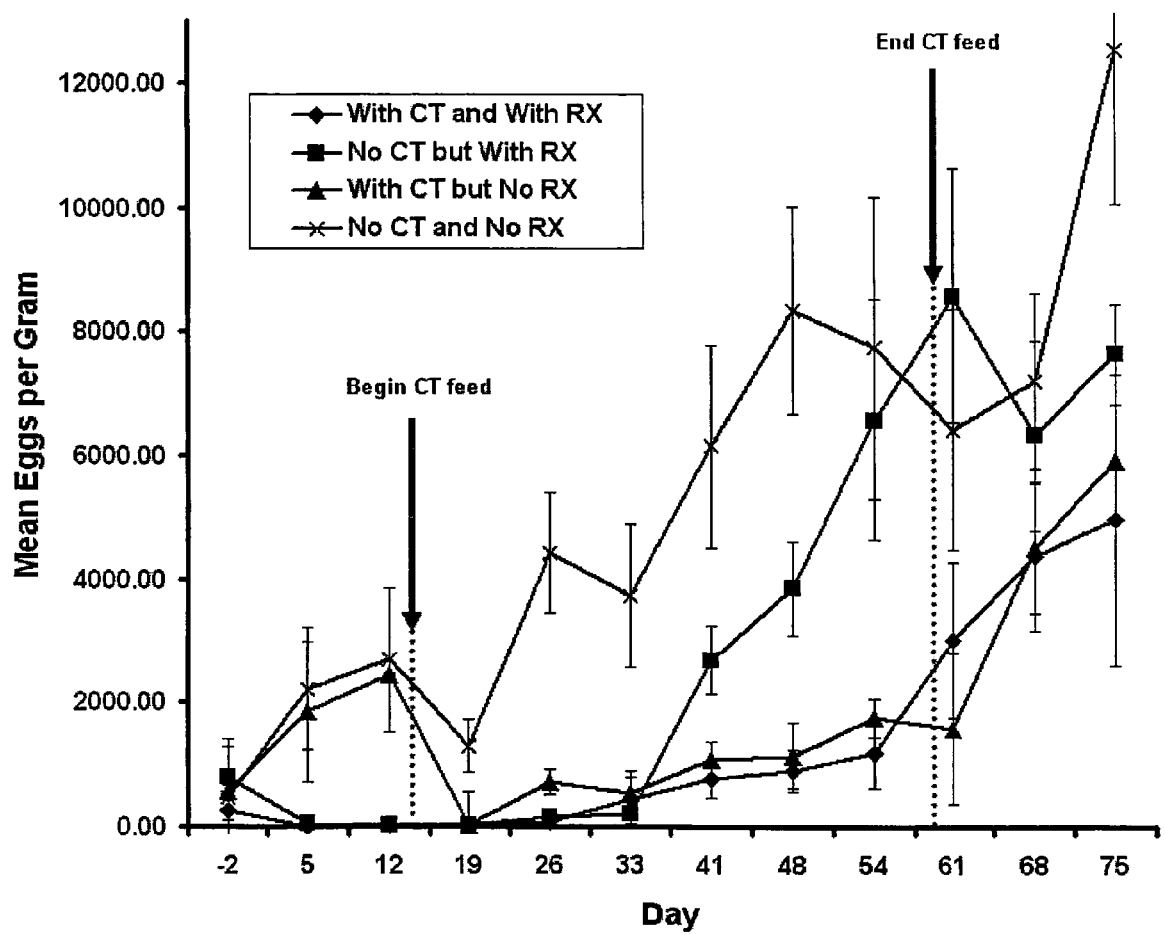
FIG. 3 is a graph of fecal egg count over time comparing the results of feeding various diets with and without *sericea lespedeza* hay to lambs infected with the nematode *Haemonchus contortus* in the experiment described in Example 2 herein.

When feeding of CT containing hay commenced on Day 14, the FEC for group 3 dropped within a week to very low levels already realized by groups 2 and 4 (FIG. 3). The reduction in FEC after introduction of CT was 97%. As trickle infections commenced at that same time, all groups saw a rise in FEC (infection levels). By Day 41, the FEC for the two groups being fed CT hay had risen more slowly than for the other two groups. FEC for sheep not eating CT hay increased 65% faster than those of the sheep in groups 3 and 4. The clear increase in all FEC around Day 41 was expected as the L3 larvae introduced one month earlier would have reached full maturity at that time. Through Day 60 as long as CT hay was being fed, the FEC remained lower in CT fed than non-CT hay fed lambs. When CT hay feeding was discontinued (Day 60), FEC in groups 3 and 4 increased substantially which indicated that the effect of CT hay was partially on fecundity of the female worms.

Figure 4:
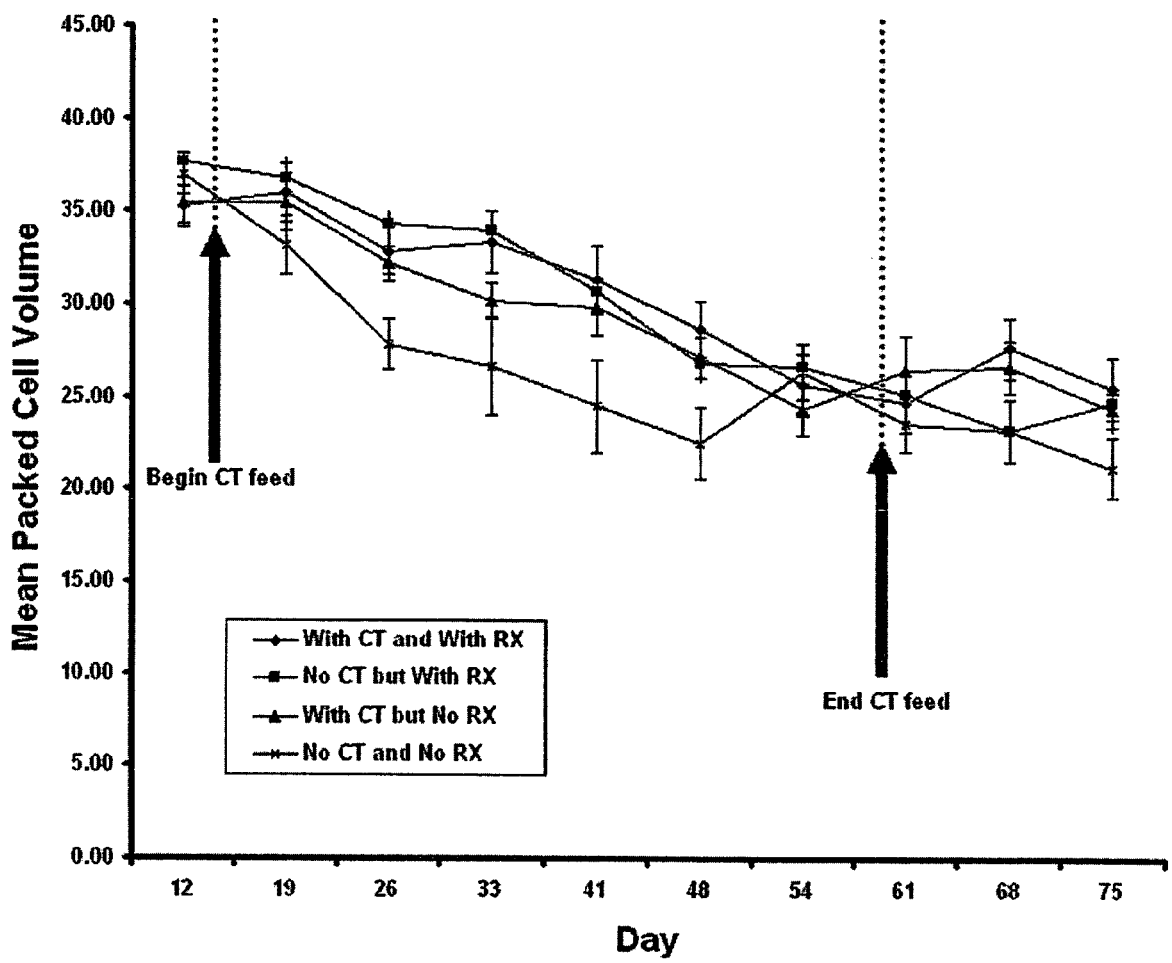
FIG. 4 is a graph illustrating blood packed cell volume over time for the lambs in the experiment of Example 2 described herein.

PCV for all animals steadily dropped as FEC increased, and tended to stabilize subsequent to Day 54 (FIG. 4). This stabilization would be expected as that would coincide with infections having reached full maturation. Also, as expected, group 1 animals had lower PCV than the other groups because they remained infected and were not dewormed. The increase in group 1 PCV on Day 54 can be attributed to one animal that required deworming otherwise it may have died. The data for that animal was not used from that point on. This indicates that the condensed tannins may slow or prevent some L3 larvae from maturing (reaching the L4 and adult stages) and thus resulting in reduced anemia.

Figure 5:
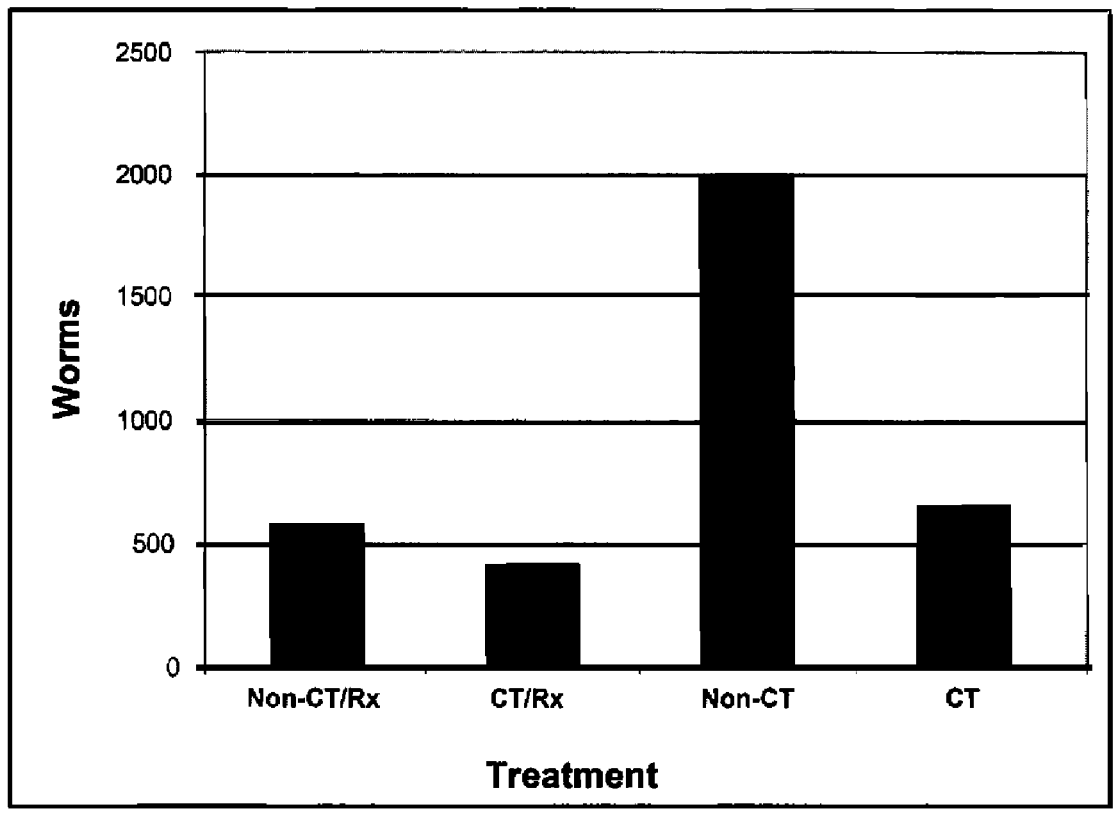
FIG. 5 is a bar graph illustrating the fecal worm count over time of the lambs treated in accordance with the diets in Example 2.

Only *H. contortus* was recovered at necropsy and worm counts showed that group 1 animals had substantially higher infections than the other 3 groups (FIG. 5). Therefore, it appears that CT hay had an effect on reducing establish worms but not so much of a effect on establishment of worms.

Conclusions

The reduction in FEC for both Groups 3 and 4 remained >75% through week seven, and then dropped substantially on weeks eight and nine after SL hay feeding was stopped. PCV tended to remain higher in the SL hay fed groups. H contortus was the most prevalent nematode in fecal cultures. Results indicated that SL, fed as hay, did effectively reduce the number of eggs (primarily *H. contortus*) shed in feces. The increase in FEC after SL hay feeding was stopped indicated that the effect was partially on nematode fecundity. Necropsy results were used to determine any effect on infection level. The average number of nematodes in SL fed and non-SL lambs was 538 and 1279, respectively. These results indicate that SL hay had a direct anthelmintic effect.

Additional observations include:

(a) *Sericea lespedeza* fed lambs fared better overall than sheep eating regular hay.

(b) Condensed tannins are shown to be highly effective against established infection of *H. contortus*.

(c) Condensed tannins may not be very effective at reducing newly acquired infection.

(d) Condensed tannins will effectively reduce pasture contamination.

TABLE 2

| Group | Anim. No. | 38138 WT | Jun. 8, 2004* FEC | Jun. 15, 2004** FEC | Jun. 22, 2004^ FEC | 6/23 Culture PCV | Hae | Coop | Trich | Oes | Jun. 29, 2004 FEC | 7/1 Culture PCV | Hae | Coop | Trich | Oes |
|---|---|---|---|---|---|---|---|---|---|---|---|---|---|---|---|---|
| Rhay Rx | 4102 | 51 | 400 | 0 | 0 | 38 | | | | | 0 | 39 | | | | |
| | 4103 | 49 | 150 | 0 | 0 | 39 | | | | | 0 | 41 | | | | |
| | 4105 | 59 | 0 | 0 | 0 | 36 | | | | | 100 | 35 | | | | |
| Group 2 | 4111 | 65 | 100 | 0 | 0 | 37 | | | | | 0 | 36 | | | | |
| | 4119 | 55 | 3250 | 250 | 200 | 38 | | | | | 100 | 36 | | | | |
| | 4128 | 46 | 850 | 0 | 0 | 38 | | | | | 0 | 34 | | | | |
| | 4202 | 75 | 50 | 0 | 0 | 35 | | | | | 0 | 38 | | | | |
| | Mean | 57.14286 | 685.71 | 35.71429 | 28.571 | 37.29 | 90 | 9 | 1 | 0 | 28.571 | 37 | 100 | 0 | 0 | 0 |
| Rhay NoRx | 4104 | 56 | 1200 | 6900 | 7100 | 35 | | | | | 2100 | 30 | | | | |
| | 4107 | 50 | 150 | 450 | 1150 | 40 | | | | | 200 | 38 | | | | |
| | 4113 | 53 | 500 | 2350 | 2400 | 36 | | | | | 2750 | 29 | | | | |
| Group 1 | 4121 | 51 | 0 | 900 | 150 | 41 | | | | | 0 | 38 | | | | |
| | 4124 | 41 | 950 | 2150 | 5150 | 35 | | | | | 1350 | 33 | | | | |
| | 4125 | 44 | 50 | 550 | 200 | 35 | | | | | 1400 | 31 | | | | |
| | 4219 | 66 | 50 | 150 | 200 | 35 | | | | | 1350 | 34 | | | | |
| | Mean | 51.57143 | 414.29 | 1921.429 | 2335.7 | 36.71 | 40 | 56 | 0 | 4 | 1307.1 | 33.29 | 51 | 35 | 4 | 10 |
| CTHay Rx | 4101 | 64 | 100 | 0 | 0 | 31 | | | | | 0 | 32 | | | | |
| | 4108 | 39 | 0 | 0 | 0 | 37 | | | | | 50 | 35 | | | | |
| | 4112 | 64 | 500 | 0 | 100 | 36 | | | | | 260 | 40 | | | | |
| Group 4 | 4123 | 31 | 900 | 0 | 0 | 38 | | | | | 0 | 39 | | | | |
| | 4129 | 40 | 0 | 0 | 0 | 35 | | | | | 0 | 31 | | | | |

TABLE 2-continued

| | | | | | | | | | | | | | | | | |
|---|---|---|---|---|---|---|---|---|---|---|---|---|---|---|---|---|
| | 4208 | 74 | 1060 | 0 | 0 | 30 | | | | | 0 | 36 | | | | |
| | 4210 | 70 | 0 | 0 | 0 | 35 | | | | | 0 | 39 | | | | |
| | Mean | 54.57143 | 425 | 0 | 14.286 | 34.57 | 86 | 15 | 0 | 0 | 42.857 | 36 | 100 | 0 | 0 | 0 |
| | % Red | | | | | | | | | | | | | | | |
| CTHay | 4109 | 47 | 50 | 50 | 100 | 31 | | | | | 0 | 35 | | | | |
| NoRx | 4115 | 49 | 0 | 0 | 50 | 38 | | | | | 0 | 40 | | | | |
| | 4117 | 58 | 250 | 3450 | 2950 | 36 | | | | | 0 | 36 | | | | |
| Group 3 | 4120 | 44 | 2100 | 5000 | 6750 | 32 | | | | | 50 | 30 | | | | |
| | 4126 | 46 | 100 | 250 | 400 | 37 | | | | | 100 | 39 | | | | |
| | 4127 | 43 | 850 | 2400 | 4450 | 39 | | | | | 0 | 33 | | | | |
| | 4220 | 64 | 400 | 2400 | 1650 | 31 | | | | | 100 | 25 | | | | |
| | Mean | 50.14286 | 535.71 | 1935.714 | 2335.7 | 34.86 | 46 | 47 | 6 | 1 | 35.714 | 34 | 47 | 33 | 5 | 15 |
| | % Red | | | | | | | | | | 97.268 | | | | | |

| Group | Anim. No. | Jul. 06, 2004 | | | | | | 7/6 Culture | | | | | 7/13 Culture | | Jul. 21, 2004 | |
|---|---|---|---|---|---|---|---|---|---|---|---|---|---|---|---|---|
| | | FEC | PCV | Hae | Coop | Trich | Oes | FEC | PCV | Hae | Coop | Trich | Oes | FEC | PCV | |
| Rhay | 4102 | 0 | 35 | | | | | 0 | 34 | | | | | 2000 | 32 | |
| Rx | 4103 | 0 | 34 | | | | | 50 | 38 | | | | | 3200 | 32 | |
| | 4105 | 300 | 35 | | | | | 200 | 32 | | | | | 1000 | 30 | |
| Group 2 | 4111 | 100 | 37 | | | | | 100 | 34 | | | | | 4750 | 32 | |
| | 4119 | 600 | 33 | | | | | 800 | 34 | | | | | 2350 | 30 | |
| | 4128 | 0 | 32 | | | | | 150 | 32 | | | | | 2200 | 28 | |
| | 4202 | 50 | 34 | | | | | 0 | 30 | | | | | 1050 | 30 | |
| | Mean | 150 | 34.29 | 100 | 0 | 0 | 0 | 185.71 | 33.43 | 91 | 0 | 9 | 0 | 2364.3 | 30.57 | |
| Rhay | 4104 | 3300 | 26 | | | | | 7500 | 26 | | | | | 2900 | 22 | |
| NoRx | 4107 | 5150 | 31 | | | | | 850 | 31 | | | | | 2300 | 30 | |
| | 4113 | 7400 | 24 | | | | | 3700 | 22 | | | | | 5600 | 23 | |
| Group 1 | 4121 | 750 | 33 | | | | | 50 | 37 | | | | | 1200 | 34 | |
| | 4124 | 6450 | 26 | | | | | 5400 | 19 | | | | | 12150 | 18 | |
| | 4125 | 3500 | 27 | | | | | 4950 | 25 | | | | | 7700 | 20 | |
| | 4219 | 700 | 35 | | | | | 3400 | 29 | | | | | 1900 | 29 | |
| | Mean | 3892.9 | 28.86 | 80 | 12 | 2 | 8 | 3692.9 | 27 | 90 | 8 | 1 | 1 | 4821.4 | 25.14 | |
| CTHay | 4101 | 0 | 35 | | | | | 0 | 36 | | | | | 0 | 38 | |
| Rx | 4108 | 0 | 29 | | | | | 0 | 34 | | | | | 0 | 28 | |
| | 4112 | 200 | 36 | | | | | 50 | 38 | | | | | 1500 | 35 | |
| Group 4 | 4123 | 0 | 33 | | | | | 2350 | 34 | | | | | 1350 | 30 | |
| | 4129 | 0 | 29 | | | | | 0 | 26 | | | | | 360 | 26 | |
| | 4208 | 750 | 32 | | | | | 650 | 35 | | | | | 450 | 30 | |
| | 4210 | 250 | 35 | | | | | 150 | 32 | | | | | 1900 | 31 | |
| | Mean | 171.43 | 32.71 | 100 | 0 | 0 | 0 | 457.14 | 33.57 | 85 | 5 | 0 | 10 | 792.86 | 31.14 | |
| | % Red | | | | | | | | | | | | | 66.465 | | |
| CTHay | 4109 | 0 | 34 | | | | | 350 | 30 | | | | | 100 | 29 | |
| NoRx | 4115 | 150 | 32 | | | | | 300 | 33 | | | | | 1450 | 32 | |
| | 4117 | 600 | 33 | | | | | 250 | 29 | | | | | 200 | 31 | |
| Group 3 | 4120 | 250 | 29 | | | | | 650 | 28 | | | | | 2550 | 24 | |
| | 4126 | 0 | 35 | | | | | 150 | 33 | | | | | 1150 | 35 | |
| | 4127 | 3350 | 30 | | | | | 1550 | 28 | | | | | 1100 | 28 | |
| | 4220 | 750 | 30 | | | | | 200 | 33 | | | | | 5350 | 29 | |
| | Mean | 728.57 | 31.86 | 64 | 22 | 3 | 11 | 492.86 | 30.57 | 76 | 4 | 2 | 18 | 1700 | 29.71 | |
| | % Red | 81.284 | | | | | | 86.654 | | | | | | 64.741 | | |

*Before deworming and used for group allocation
**After deworming (6/10-11) with LEV/ABZ
^Start trial: Start CT feeding & inoculate each animal with 500 L3 3 times/wk

EXAMPLE 3

Introduction

The major advantages of hay over fresh CT forage are increased flexibility in storage and transport, as well as timing/season of feeding. The objective of the current investigation was to determine the effects of feeding SL hay on the egg, larval, and adult stages of GIN in goats fed in confinement.

Materials and Methods

Experimental Design and Protocol:
A confinement feeding trial was conducted using 20 weaned intact Boer male goats (6-8 months old; 23±2.83 kg) at the Fort Valley State University (FVSU) Agricultural Research Station, Fort Valley, Ga. Goats were housed in 4 pens (5 animals/pen) on concrete in a covered barn with open sides. Area of each pen was 9.3 $m^2$, with similar temperature and sunlight conditions. Prior to confinement, the animals were grazed for 4 weeks on bermudagrass (BG) pasture to allow development of a low-level GIN infection. In addition, starting 2 weeks before moving to the pens, and then for 8 weeks during the trial, the GIN infection level of individual animals was boosted with 500 *H. contortus* larvae three times a week to simulate natural infection.

Experimental Diets:
After being moved to the pens, body weights were recorded, and all the goats were given access to BG hay at 80% of daily intake, a 16% crude protein feed supplement (ground corn, soybean meal, poultry fat, trace mineral salt and vitamin premix; Table 3) at 20% of daily intake, and ad libitum water. After a 2-week adjustment period, the goats were stratified by FEC and randomly assigned to 2 treatment groups (n=10) in 4 pens (5 goats per pen, 2 treatment and 2 control pens). All goats were continued on the BG (control) ration for 3 additional weeks to allow infection levels to increase. After this time, the control animals were continued on the BG hay diet, whereas the treatment group was switched to the SL hay diet for 6 weeks. Based on the composition of BG (13.3% CP) and SL (12.6% CP), separate supplements were formulated to balance for CP. Hay for both treatments was fed at 3.5% BW throughout the trial, allowing approximately 25% feed refusals. Both diets consisted of approximately 80% hay and 20% supplement. (729 g BG and 250 g supplement/animal; 700 g SL and 280 g supplement/animal daily).

Analysis of Hay Samples:

Samples of SL and BG hay were ground in a Wiley Mill to pass a 1 mm screen and then analyzed for N and CT content. Nitrogen analysis was completed using a Truspec C/N analyzer (Leco Corporation, St. Joseph, Mich.), while extractable, protein-bound, and fiber-bound CT content was determined by the Terrill et al. (1992) method using purified quebracho CT as the standard (Kahiya et al., 2003).

Sampling Procedures and Analysis:

Throughout the 11-week confinement trial (5-week pretrial, 6-week trial periods), fecal and blood samples were collected weekly from individual animals for FEC and packed cell volume (PCV) analysis, respectively. Feces were collected rectally, with ova counted using a modified McMaster procedure (Hansen and Perry, 1994). Data were expressed as eggs per gram (EPG) of feces. Blood samples were taken by jugular venipuncture into EDTA-vacutainer tubes, with PCV determined using a micro-haematocrit centrifuge and reader. Fecal cultures were prepared weekly on pooled samples from control and treatment goats as described by Terrill et al. (2004) to allow counting and identification of nematode larvae to species. Percentage GIN larval development was calculated by the following formula:

Percentage Larval development=(number of larvae/g feces)/(eggs/g feces)×100.

Recovery and Counting of Adult Nematodes:

At the end of the trial, the goats were slaughtered at the USDA-approved abattoir at the FVSU Agricultural Research Station, and adult worms recovered from the abomasum and small intestine (Hansen and Perry, 1994). Body weights were recorded pre-slaughter, and fecal and blood samples taken from individual animals for FEC and PCV determination, respectively. After slaughter, the abomasum and small intestine of each goat were ligated, opened, and the contents washed into plastic buckets. For each sample type, the contents were brought up to 3 L with tap water, thoroughly mixed, and then two 5% aliquots (150 mL) taken into 250-mL storage containers. Approximately 100 mL of formalin (5%) was added to each aliquot as a preservative. For both abomasal and small intestinal samples, the worms in one aliquot were washed on a mesh screen (No 270) with tap water, the formalin discarded, and the nematodes recovered into a 50 mL centrifuge tube. All the nematodes in the tube were then counted and identified to species and sex using a phase contrast microscope.

Statistical Analysis:

The egg count and PCV data were analyzed as a randomized block design using repeated measured analysis with pen, treatment, and time in the model and pretrial and trial periods analyzed separately (SAS, 1992). Percentage larval recovery and % *H. contortus* data from pooled fecal cultures were analyzed using repeated measures analysis with treatment and time in the model and pretrial and trial periods analyzed separately. Adult worm data were analyzed using GLM procedure in SAS (1992) with treatment and pen as independent variables.

Results

CT Levels in SL Hay:

The extractable, protein-bound, and fiber-bound CT concentrations in the SL hay were 3.6, 13.4, and 5.4%, respectively, with a total CT concentration (extractable+protein-bound+fiber-bound) of 22.4%.

Figure 6:
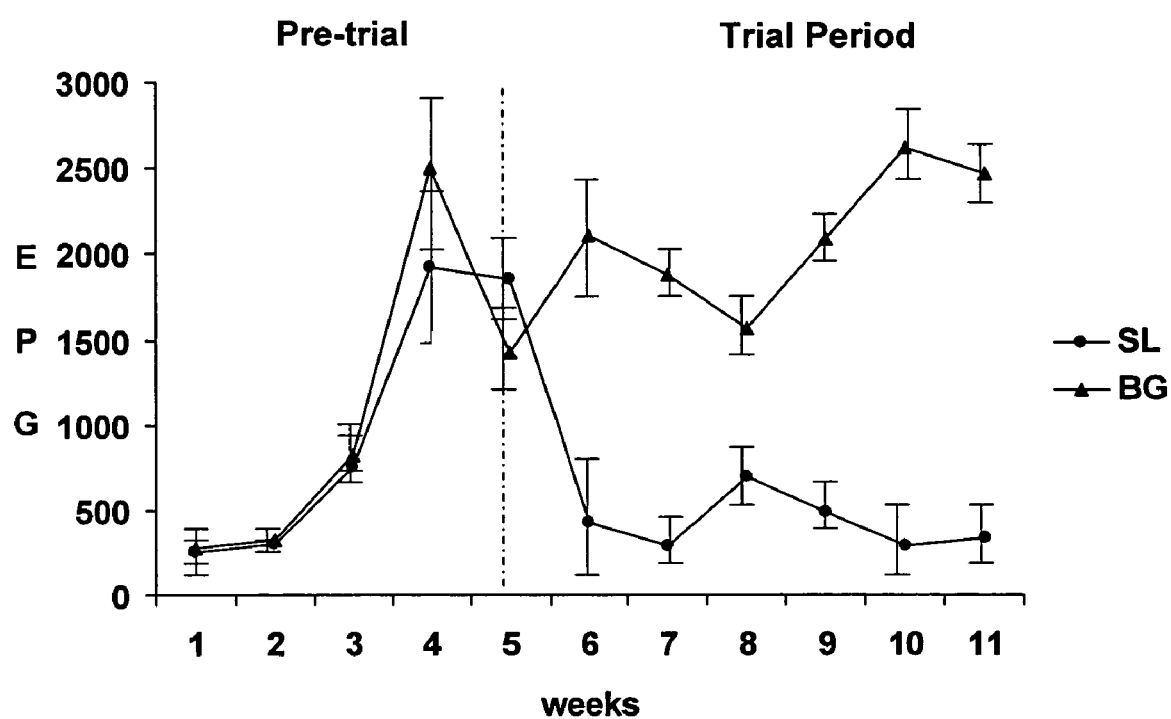
FIG. 6 is a graph illustrating the effect of feeding *sericea lespedeza* (SL) hay or bermudagrass (BG) hay on the nematode fecal egg count expressed in eggs per gram (EPG) of feces over time for the goats treated in accordance with the diets of Example 3 described herein.

Fecal Egg Counts:

Egg counts were similar between the two groups during the pre-trial, with EPGs increasing from approximately 250 to 2500 in all animals during this period (FIG. 6). During the 6-week trial period, treatment, time, and treatment×time effects were all significant (P<0.01). Egg counts dropped by 79.7% one week after sericea feeding was started, and the reduction increased to approximately 88% over the last two weeks of the trial period (FIG. 6).

Figure 7:
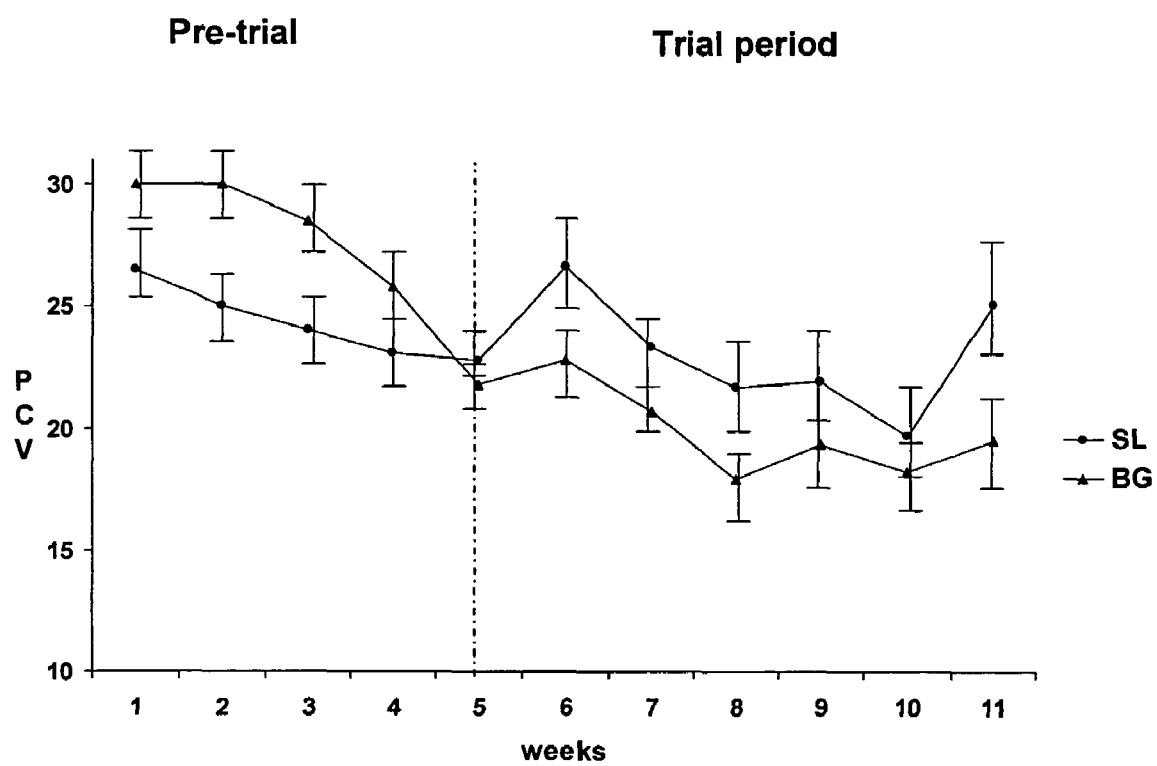
FIG. 7 is a graph illustrating the effect of feeding *sericea lespedeza* (SL) hay or bermudagrass (BG) hay on the blood packed cell volume (PCV) over time for the goats treated in Example 3.

Blood Packed Cell Volume:

Treatment and time main effects were significant (P<0.01) for PCV data. During the pre-trial, PCV was higher (P<0.01) in BG animals (27.2) than in SL goats (24.3), while PCV was higher (P<0.01) in the SL group than in the BG animals during the trial period (23.1 vs. 19.7, respectively) (FIG. 7). The significant time effect was due to variation in PCV data from both SL and BG groups throughout the trial period.

Figure 8:
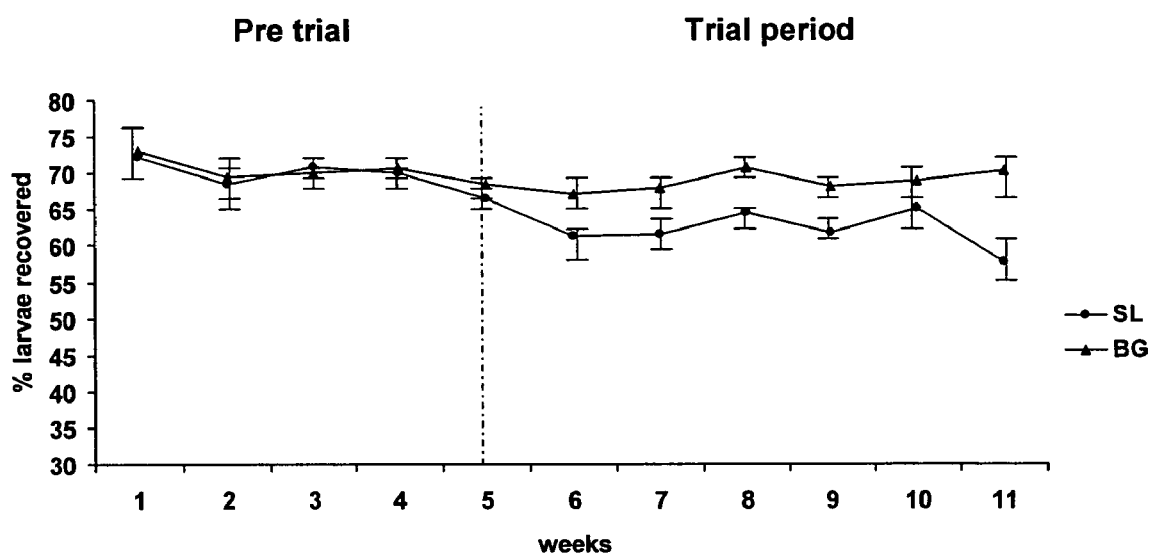
FIG. 8 is a graph illustrating the effect of feeding *sericea lespedeza* (SL) hay or bermudagrass (BG) hay on the fecal nematode larvae recovered over time for the goats treated in Example 3.

Percentage Larvae Recovered from Fecal Cultures:

Percentage larvae recovered from fecal cultures was similar between SL and BG groups during the pretrial period (73.1 and 71.3%, respectively), whereas treatment, time, and treatment×time effects were significant (P<0.01) for larval recovery data during the trial period. The larvae recovered from fecal cultures from SL-fed goats decreased from 61.2 to 57.7% during the trial period, whereas the BG group increased from 64.3 to 70.3% during this period (FIG. 8).

Figure 9:
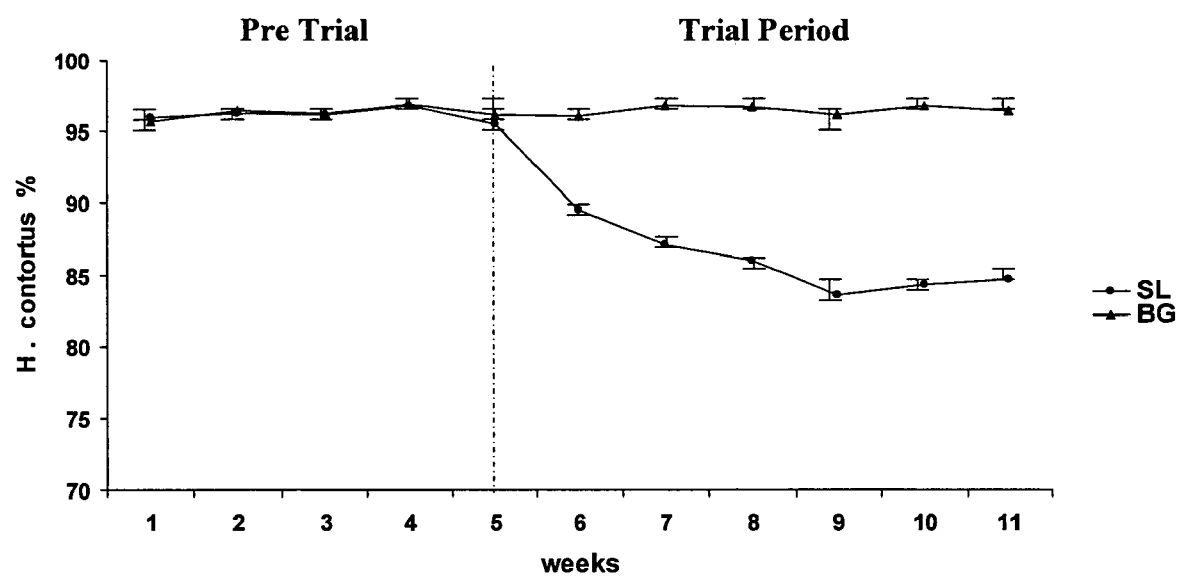
FIG. 9 is a graph illustrating the effect of feeding *sericea lespedeza* (SL) hay or bermudagrass (BG) hay on the percent *Haemonchus contortus* larvae contained in the total nematode larvae recovered over time for the goats treated in Example 3.

Percentage *H. contortus* Recovered from Fecal Cultures:

Throughout the pretrial period, treatment and control groups had similar levels of *H. contortus* in fecal cultures (95.9 and 95.7%, respectively). During the trial period, treatment, time, and treatment×time effects were all significant (P<0.01) for % *H. contortus* larvae recovered in cultures. In the fecal cultures from BG-fed goats, the % *H. contortus* consistently remained 96-97% throughout the trial period, whereas in SL-fed goats, % *H. contortus* dropped to 89.5% after a week, 86% after three weeks, and 84.7% by the end of the trial period (FIG. 9).

Adult Nematodes:

The number of adult nematodes in both the abomasum and the small intestines was lower (P<0.001) in goats fed SL compared with BG hay (Table 4). Abomasal worms included *H. contortus* and *Osteragia circumcincta*, while all the small intestinal worms identified were *Trichostongylus colubriformis*. The SL diet reduced the total count (P<0.001) and number of males (P<0.05) and females (P<0.01) of all three of these species in the goats, compared with animals fed the BG diet. Also, for all three species, there was a greater reduction in the number of female worms compared with males (Table 4).

Discussion

Feeding of SL hay appears to be an effective means of controlling *H. contortus* infection in goats. These results confirm reports on anthelmintic effects of grazed SL pastures in goats. Min et al (2004) reported 71.7% reduction in FEC in goats grazing SL pastures compared with annual grass pasture. These authors suggested that the primary effect of SL in the diet is reduction in fecundity, or egg-laying of adult worms rather than direct killing of the worms. The results of the current study show that the anthelmintic effect of SL hay is primarily a direct effect on the worms, based upon much lower numbers of both abomasal and small intestinal nematodes in the goats on the SL hay diet. Similar results have been observed with sheep fed a SL hay diet. Lange et al (2005) reported reduced FEC and worm counts in sheep fed SL hay compared with BG hay in a confinement feeding study completed in Louisiana.

Other authors have reported anthelmintic effects of dried CT forages fed to goats, including reduced FEC in animals given sainfoin hay (Paolini et al., 2003), and reduced FEC and worm counts in goats provided dried *Acacia karoo* foliage (Kahiya et al., 2003). The nematocidal effects of SL hay were greater than the effects reported in these studies, which may be related to the different types of CT in these plant species. All of these plants contain relatively high levels of CT (Terrill et al., 1989; Kahiya et al., 2003), but the reactivity of the CT may differ. This is supported by reports on nutritional effects of different CT types. For example, variable effects of CT on plant protein degradation have been observed in sheep fed forage from two different *Lotus* species. At similar CT concentrations (0.25 to 1.75 mg of CT/mg of total soluble plant protein), *Lotus pedunculatus* CT was more effective at protecting plant protein from degradation by rumen microorganisms than *Lotus corniculatus* CT (Aerts et al., 1999). The CT in *L. pedunculatus* is higher in MW and has a higher ratio of prodelphinidin to procyanidin subunits than *L. corniculatus* CT (Foo et al., 1996; 1997). This ratio is higher in the CT from SL than from most other legumes (Burns, 1966). It appears that as with protein degradation, the chemical structure of CT, as well as its concentration, needs to be considered in studies involving GIN control.

The reactivity of the CT of SL may also explain why this forage maintains its anthelmintic properties when fed as hay. Drying a CT forage reduces the proportion of tannin that is extractable using an aqueous solvent and increases the proportion that is bound to protein (Terrill et al., 1992). The unbound, or 'free' CT is more reactive than bound forms (Barry and Manley, 1986). Although the extractable CT level is lower in SL hay than in grazed forage, the anthelmintic effects observed with goats fed the hay in confinement were comparable with reports from grazing studies (Min and Hart, 2003; Min et al., 2004). This suggests that the particular type of CT in the plant is more critical for controlling GIN than the total concentration of bound and unbound forms in the diet.

Effects of drying on CT forms in forage are important from a nutritional standpoint in animals, and this needs to be considered with SL. This plant has been declared a noxious weed in parts of the Midwest because it is not considered palatable to grazing beef cattle. Too high a level of CT in the diet can reduce intake and digestibility of the forage (Terrill et al., 1989; Barry and Manley, 1986). Terrill et al (1989) reported lower intake and digestibility of fresh-frozen high-tannin SL compared with a low-tannin type fed to sheep. These differences were lost when then fresh forages were sun-dried and fed as hay. Reduced intake of SL does not appear to be a problem with grazing goats (Min and Hart., 2003). Also, despite differences in willingness of different animal species to graze SL, sheep, goats, cattle, and horses all readily consume SL hay (C. S. Hoveland, pers. comm.).

Conclusion

Feeding SL hay to goats can effectively reduce nematode parasite infection levels through direct anthelmintic effects on the adult worms in the gastrointestinal tract and by reducing parasite egg viability and/or larval development in feces. As SL is a crop that is well-adapted to the southern US, growing this plant for hay or grazing as a natural deworming agent may be a cost-effective, environmentally-friendly alternative/addition to the exclusive use of chemical anthelmintics by small ruminant producers in this region.

REFERENCES

Aerts, R. J., McNabb, W. C, Molan, A., Brand, A., Peters, J. S., Barry, T. N., 1999. Condensed tannins from *Lotus corniculatus* and *Lotus pedunculatus* affect the degradation of ribulose 1,5-bisphosphate carboxylase (Rubisco) protein in the rumen differently. J. Sci. Food Agric. 79, 79-85.

Barry, T. N., Manley, T. R., 1986. Interrelationships between the concentrations of total condensed tannin, free condensed tannin and lignin in *Lotus* sp. and other possible consequences in ruminant nutrition. J. Sci. Food Agric. 37, 248-254.

Barry, T. N., McNeill, D. M., McNabb, W. C., 2001. Plant secondary compounds; their impact on nutritive value and upon animal production. Pages 445-452 in Proc. XIX Int. Grass. Conf., Sao Paulo, Brazil.

Burns, R. E., 1966. Tannin in *sericea lespedeza*. Bull. 164. Georgia Agric. Exp. Sta., Athens, Ga.

Burke, J. M., Miller, J. E., Olcott, D. D., Olcott, B. M., Terrill, T. H., 2004. Effect of copper oxide wire particles dosage and feed supplement level on *Haemonchus contortus* infection in lambs. Vet. Parasitol. 123, 235-243.

Chartier, C., Etter, E., Heste, H., Pors, I., Koch, C., Dellac, B., 2000. Efficacy of copper oxide needles for the control of nematode parasites in dairy goats. Vet. Res. Commun. 24, 389-399.

Foo, L. Y., Newman, R., Waghorn, G. C., McNabb, W. C., Ulyatt, M. J., 1996. Proanthocyanidins from *Lotus corniculatus*. Phytochem. 41, 617-621.

Foo, L. Y., McNabb, W. C., Waghorn, G. C., Ulyatt, M. J., 1997. Proanthocyanidins from *Lotus pedunculatus*. Phytochem. 45, 1689-1696.

Haenlein. G. F. W., 1992. Alternatives in dairy product market. Proc. Sheep and Goat Industry Devel. Symp (A.D-.Scarfe. ed.), Tuskegee University, AL.

ansen, J., Perry, B., 1994. The epidemiology, diagnosis and control of helminth parasites of ruminants: A handbook. International Livestock Research Institute, Nairobi, Kenya.

Haslem, E., 1989. Plant Polyphenols—Vegetable Tannins. Cambridge Univ. Press, U.K.

Hoveland, C. S., Windham, W. R., Boggs, D. L., Durham, R. G., Calvert, G. V., Newsome, J. F., Dobson, J. W., Jr., Owsley, M., 1990. *Sericea lespedeza* production in Georgia. The Georgia Exp. Sta. Res. Bull. 393.

Kahiya. C., Mukaratirwa, S., Thamsborg, S. M., 2003. Effects of *Acacia nilotica* and *Acacia karoo* diets on *Haemonchus contortus* infection in goats. Vet. Parasitol. 115, 265-274.

Knox, D. P., 2000. Development of vaccines against gastrointestinal nematodes. Parasitol. 120, 43-61.

Knox, D. P., Smith, W. D., 2001. Vaccination against gastrointestinal nematode parasites of ruminants using gut-expressed antigens. Vet. Parasitol. 100, 21-32.

Lange, K., Olcott, D., Miller, J. E, Mosjidis, J. A., Terrill, T. H., Burke, J. M., 2005. Effect of the condensed tannin-containing forage, *sericea lespedeza*, fed as hay, on natural and experimental challenge infection in lambs. Abst. Southern Sec. ASAS Meetings, Little Rock, Ark., pages 15-16.

Larsen M., 2000. Prospects for controlling animal parasitic nematodes by predacious micro fungi. Parasitol. 120, S120-S131.

Maxey, K., 1993. Year of progress. Dairy Goat J. 11, 32.

Miller, J. E., 1996. Controlling goat parasites in the Southeast. p 80-82 In Proceedings of the Southeast Regional Meat Goat Production Symposium "Meat goat production in the Southeast—today and tomorrow', 21-24 Feb., 1996, Florida A&M University, Tallahassee, Fla.

Min, B. R., Hart, S. P., 2003. Tannins for suppression of internal parasites. J. Anim. Sci. 81(E. Suppl. 2), E102-E109.

Min, B. R., McNabb, W. C., Barry, T. N., Kemp, P. D., Waghorn, G. C., McDonald, M. F., 1999. The effect of condensed tannins in *Lotus corniculatus* upon reproductive efficiency and wool production in sheep during late summer and autumn. J. Agric. Sci. 132,323-334.

Min, B. R., Pomroy, W. E., Hart, S. P., Sahlu, T., 2004. The effect of short-term consumption of a forage containing condensed tannins on gastro-intestinal nematode parasite infections in grazing wether goats. Small Rumin. Res. 51, 279-283.

Molan, A. L., Waghorn, G. C., McNabb, W. C., 1999. Condensed tannins and gastro-intestinal parasites in sheep. Proc. NZ Grassl. Assoc. 61, 57-61.

Molan, A. L., Waghorn, G. C, Min, B. R., McNabb, W. C., 2000. The effect of condensed tannins from seven herbages on *Trichostrongylus colubriformis* larval migration in vitro. Folia Parasitol. 47:39-44.

Mortensen, L. L., Williamson, L. H., Terrill, T. H., Kircher, R. A., Larsen, M., Kaplan, R. M., 2003. Evaluation of prevalence and clinical implications of anthelmintic resistance in gastrointestinal nematodes in goats. JAVMA 223, 495-500.

Niezen, J. H., Charleston, W. A. G., Robertson, H. A., Shelton, D, Waghom, G. C., Green, R., 2002. The effect of feeding sulla (*Hedysarum coronarium*) or Lucerne (*Medicago sativa*) on lamb parasite burdens and development of immunity to gastrointestinal nematodes. Vet. Parasitol. 105, 229-245.

Niezen, J. H., Waghorn, T. S., Charleston, W. A. G., Waghorn, G. C., 1995. Growth and gastrointestinal parasitism in lambs grazing one of seven herbages and dosed with larvae for six weeks. J. Agric. Sci. 125, 281-289.

Paolini, V., Dorchies P., Hoste H., 2003. Effects of sainfoin hay on gastrointestinal infection with nematodes in goats. Vet. Record 152, 600-601.

Pinkerton, F., Escobar, E. N., Harwell, L., Drinkwater, W., 1994. A survey of prevalent production and marketing practices in meat goats of southern origin. Langston Univ. Goat Res. Ext. Newsletter 182, 1-47.

SAS Institute, 1992. SAS/STAT Software: changes and enhancements. Release 6.07, SAS Technical Report, SAS Institute, Cary, N.C.

Shaik, S. A., Terrill., T. H., Miller, J. E., Kouakou, B., Kannan, G., Kallu, R. K., Mosjidis, J. A., 2004. Effects of feeding *sericea lespedeza* hay to goats infected with *Haemonchus contortus*. SAJ Anim. Sci. 34, 234-236.

Terrill T H, Kaplan, R. M., Larsen, M., Samples, O. M., Miller, J. E., Gelaye, S., 2001. Anthelmintic resistance on goat farms in Georgia: efficacy of anthelmintics against gastrointestinal nematodes in two selected goat herds. Vet. Parasitol. 97, 261-268.

Terrill, T. H., Larsen, M., Samples, O. M., Husted, S., Miller, J. E., Kaplan, R. M., Gelaye, S., 2004. Capability of the nematode-trapping fungus *Duddingtonia flagrans* to reduce infective larvae of gastrointestinal nematodes in goat feces in the southeastern United States: dose titration and dose time interval studies. Vet. Parasitol. 120, 285-296.

Terrill, T. H., Rowan, A. M., Douglas, G. B., Barry, T. N., 1992. Determination of extractable and bound condensed tannin concentrations in forage plants, protein concentrate meals, and cereal grains. J. Sci. Food Agric. 58, 321-329.

Terrill, T. H., Windham, W. R., Hoveland, C. S., Amos, H. E., 1989. Influence of forage preservation method on tannin concentration, intake and digestibility of *sericea lespedeza* by sheep. Agron. J. 81, 435-439.

TABLE 3

Constituents of 16% crude protein supplemental feed offered to parasitized goats at 20% of daily intake

| Feed constituent | % |
|---|---|
| Corn | 63.58 |
| Soybean meal | 28.45 |
| Poultry fat | 3.98 |
| Trace mineral salt[a] | 1.99 |
| Vitamin Premix[b] | 1.99 |

[a]Contains 95 to 98% NaCl and at least 0.05% Mg, 0.032% Cu, 0.005% Zn, 0.24% Fe, 0.011% Co, 0.007% I and 0.24% Mn.
[b]Contains at least 2,200 IU vitamin A, 1,200 IU vitamin $D_3$ and 2.2 IU vitamin E per gram.

TABLE 4

Total male and female nematodes in abomasum and small intestine of parasitized goats fed sericea lespedeza (SL) or bermudagrass (BG) hay and a small amount of concentrates.

| | Diet | | | |
|---|---|---|---|---|
| Adult nematodes | BG | SL | SEM | P < |
| Abomasum (total) | 3450[a] | 1359[b] | 70 | 0.001 |
| *H. contortus* | 2728[a] | 834[b] | 68 | 0.001 |
| Male | 1269[a] | 491[b] | 25 | 0.001 |
| Female | 1459[a] | 343[b] | 49 | 0.001 |
| *O. circumcincta* | 712[a] | 525[b] | 22 | 0.001 |
| Male | 318[a] | 273[b] | 12 | 0.05 |
| Female | 394[a] | 252[b] | 20 | 0.01 |
| Small Intestine (total) | 949[a] | 571[b] | 39 | 0.001 |
| *T. colubriformis* | 949[a] | 571[b] | 39 | 0.001 |
| Male | 417[a] | 305[b] | 25 | 0.01 |
| Female | 532[a] | 266[b] | 22 | 0.001 |

[a,b]Row means with unlike superscripts differ significantly.

EXAMPLE 4

To determine the level of SL needed to reduce GIN infection, a confinement study was completed with 32 Spanish/Boer/Kiko cross yearling bucks offered 1 of 4 diets consisting of 75% hay and 25% concentrate (n=8, 4 goats/pen). The hay portion of each diet consisted of a combination of ground SL (0, 25, 50, and 75% of the diet) and bermudagrass [BG, *Cynodon dactylon* (L.) Pers.; 75, 50, 25, and 0% of the diet]. The bucks were allowed to acquire a natural GIN infection on pasture prior to moving to the pens. After a 3-week adjustment period in the pens, the goats were stratified by fecal egg count (FEC), randomly assigned to treatments and pens, and then fed the treatment diets for 6 weeks. During the experimental period, fecal and blood samples were collected from individual animals weekly to determine FEC and blood packed cell volume (PCV), respectively. Goats fed SL hay at 25, 50 and 75% of the diet had lower (P<0.05) FEC than control animals (75% BG hay), with a greater reduction as % SL in the diet increased. There was also a dose response for PCV, with 75% SL-fed goats having higher PCV (P<0.10) than the 25% SL and control animals, while the 50% SL goats were intermediate. The optimum level of SL hay in the diet for reducing GIN infection of small ruminants appears to be 50-75%, with some benefit even at 25% of the diet. Ground SL hay has excellent potential as an all-natural supplement/replacement for chemical anthelmintics.

TABLE 5

Nematode egg count in feces of parasitized goats fed four different levels of ground sericea *lespedeza* or bermudagrass hay and a small amount of concentrates.

| Diet[1] | | | Sampling Date | | | | | | |
|---|---|---|---|---|---|---|---|---|---|
| % SL | % BG | % SP | 1 | 2 | 3 | 4 | 5 | 6 | 7 |
| | | | Nematode egg count per gram feces | | | | | | |
| 0 | 75 | 25 | 2033$^a$ | 2900$^a$ | 2100$^a$ | 3383$^a$ | 1717$^a$ | 1667$^a$ | 3516$^a$ |
| 25 | 50 | 25 | 2140$^a$ | 3200$^a$ | 1930$^a$ | 1850$^b$ | 1260$^{ab}$ | 2410$^a$ | 2340$^a$ |
| 50 | 25 | 25 | 1770$^a$ | 2680$^a$ | 1420$^a$ | 1140$^b$ | 930$^{ab}$ | 970$^b$ | 540$^b$ |
| 75 | 0 | 25 | 1807$^a$ | 2029$^a$ | 1479$^a$ | 864$^b$ | 607$^b$ | 1114$^{ab}$ | 286$^b$ |
| SE | | | 447 | 521 | 626 | 409 | 331 | 461 | 617 |

[1]P % SL = percentage sericea *lespedeza*; % BG = percentage bermudagrass; % SP = percentage supplement.
$^{a,b,c}$Column means with unlike superscripts differ (P < 0.05).

TABLE 6

Blood packed cell volume of parasitized goats fed four different levels of ground sericea *lespedeza* or bermudagrass hay and a small amount of concentrates.

| Diet[1] | | | Sampling Date | | | | | | |
|---|---|---|---|---|---|---|---|---|---|
| % SL | % BG | % SP | 1 | 2 | 3 | 4 | 5 | 6 | 7 |
| | | | Blood packed cell volume | | | | | | |
| 0 | 75 | 25 | 16.6$^a$ | 18.7$^a$ | 21.4$^{ab}$ | 20.7$^a$ | 18.3$^{ab}$ | 18.8$^a$ | 19.5$^a$ |
| 25 | 50 | 25 | 17.0$^a$ | 17.2$^a$ | 17.3$^b$ | 16.8$^a$ | 17.7$^b$ | 18.1$^a$ | 18.1$^a$ |
| 50 | 25 | 25 | 18.0$^a$ | 16.3$^a$ | 19.0$^{ab}$ | 19.9$^a$ | 19.3$^{ab}$ | 22.3$^{ab}$ | 22.8$^{ab}$ |
| 5 | 0 | 25 | 20.0$^a$ | 21.0$^a$ | 24.7$^a$ | 23.3$^a$ | 24.2$^a$ | 25.3$^b$ | 28.3$^b$ |
| SE | | | 2.0 | 2.4 | 2.6 | 2.5 | 2.3 | 2.3 | 2.8 |

[1]P % SL = percentage sericea *lespedeza*; % BG = percentage bermudagrass; % SP = percentage supplement.
$^{a,b,c}$Column means with unlike superscripts differ (P < 0.10).

We claim:

1. A method of controlling gastrointestinal nematode infections in an animal, comprising feeding the animal an animal feed composition comprising:
    (a) meal; and
    (b) an effective amount of *Sericea lespedeza* dry hay for controlling gastrointestinal nematode infections in the animal, wherein the composition comprises 25-80% *Sericea lespedeza* hay on a dry weight basis.

2. The method of claim 1, wherein the composition comprises 50-75% *Sericea lespedeza* hay on a dry weight basis.

3. The method of claim 1, wherein the animal is selected from the group consisting of a ruminant, a pseudoruminant, a horse, a swine, a laboratory mammal, an exotic hoofstock, a domestic mammal, and poultry.

4. The method of claim 3, wherein the ruminant is selected from the group consisting of cattle, a sheep, a goat, a bison and a deer.

5. The method of claim 3, wherein the pseudoruminant is selected from the group consisting of a camel, a llama, an alpaca and a vicuna.

6. The method of claim 3, wherein the laboratory mammal is selected from the group consisting of a rabbit, a rat, a mouse, a hamster and a gerbil.

7. The method of claim 3, wherein the exotic hoofstock is selected from the group consisting of a giraffe, a black buck, an antelope, a kudu and a zebra.

8. The method of claim 3, wherein the domestic mammal is selected from the group consisting of a cat and a dog.

9. The method of claim 3, wherein the poultry is selected form the group consisting of a chicken, a turkey, a duck, a goose, a pheasant and a quail.

10. The method of claim 1, wherein the composition further includes an effective amount of an anthelmintic agent.

11. The method of claim 10, wherein the anthelmintic agent is selected from the group consisting of Fenbendazole, Ivermectin, Doramectin, Mixodectin, Levamisole and Albendazole.

12. The method of claim 1, wherein the nematode is selected from the group consisting of *Haemonchus, Trichostrongylus, Ostertagia, Teladorsagia, Cooperia, Spiculoptertagia, Nematodirus, Bunostomum,* and *Oesophagostomum*.

13. The method of claim 1, wherein the method is effective for reducing fecal egg counts by at least 79.7% in the animal.

14. The method of claim 1, wherein the animal feed composition comprises pellets, cubes, blocks or briquettes comprising the meal and the *Sericea lespedeza* dry hay.

15. A method of controlling gastrointestinal nematode infections in animals, comprising the steps of:
    (a) providing meal;
    (b) incorporating with the meal an effective amount of *Sericea lespedeza* dry hay for controlling gastrointestinal nematode infections to form a feed composition, wherein the composition comprises 25-80% *Sericea lespedeza* hay on a dry weight basis; and
    (c) feeding the feed composition to an animal.

16. The method of claim 15, wherein the composition comprises 50-75% *Sericea lespedeza* hay on a dry weight basis.

17. The method of claim 15, wherein the animal is selected from the group consisting of a ruminant, a pseudoruminant, a horse, a swine, a laboratory mammal, an exotic hoofstock, a domestic mammal, and poultry.

18. The method of claim 17, wherein the ruminant is selected from the group consisting of cattle, a sheep, a goat, a bison and a deer.

19. The method of claim 17, wherein the pseudoruminant is selected from the group consisting of a camel, a llama, an alpaca and a vicuna.

20. The method of claim 17, wherein the laboratory mammal is selected from the group consisting of a rabbit, a rat, a mouse, a hamster and a gerbil.

21. The method of claim 17, wherein the exotic hoofstock is selected from the group consisting of a giraffe, a black buck, an antelope, a kudu and a zebra.

22. The method of claim 17, wherein the domestic mammal is selected from the group consisting of a cat and a dog.

23. The method of claim 17, wherein the poultry is selected form the group consisting of a chicken, a turkey, a duck, a goose, a pheasant and a quail.

24. The method of claim 15, wherein the composition further includes an effective amount of an anthelmintic agent.

25. The method of claim 24, wherein the anthelmintic agent is selected from the group consisting of Fenbendazole, Ivermectin, Doramectin, Mixodectin, Levamisole and Albendazole.

26. The method of claim 15, wherein the nematode is selected from the group consisting of *Haemonchus, Trichostrongylus, Ostertagia, Teladorsagia, Cooperia, Spiculoptertagia, Nematodirus, Bunostomum,* and *Oesophagostomum.*

27. The method of claim 15, wherein the method is effective for reducing fecal egg counts by at least 79.7% in the animal.

28. The method of claim 15, further comprising forming the feed composition into a discrete shape prior to (c) feeding the feed composition to the animal.

29. The method of claim 28, wherein said discrete shape is formed by extruding the feed composition.

30. The method of claim 28, wherein the discrete shape is formed by compacting the feed composition.

31. The method of claim 28, wherein the discrete shape is selected from the group consisting of pellets, cubes, blocks and briquettes.

* * * * *